United States Patent [19]

Glenn

[11] Patent Number: 5,503,973
[45] Date of Patent: Apr. 2, 1996

[54] METHOD FOR INHIBITION OF VIRAL MORPHOGENESIS

[75] Inventor: Jeffrey Glenn, San Francisco, Calif.

[73] Assignee: The Regents of the University of California, Oakland, Calif.

[21] Appl. No.: 890,754

[22] Filed: May 29, 1992

[51] Int. Cl.⁶ .............................. C12Q 1/70; C12N 7/01; C12N 7/04; A61K 35/76
[52] U.S. Cl. .......................... 435/5; 435/235.1; 435/236; 435/172.3; 424/93.2; 424/93.6; 514/2
[58] Field of Search .................... 435/4, 5, 6, 235.1, 435/236, 172.3; 424/89, 93.2, 93.6; 514/2

[56] References Cited

U.S. PATENT DOCUMENTS

H1,345   8/1994   Biller ..................................... 514/108

OTHER PUBLICATIONS

Koff, T.; Gastroenterology (1992) 103:1978–1986; Prenylation of the large hepatitis delta virus antigen: A target for antiviral therapy.
Overmeyer, et al.; J. Biol. Chem. (1992) 267(31)22686–22692; Isopernoid requirement for intracellular transport and processing of murine leukemia virus envelope protein.
Hoffman M., Science (1991) 254:650–651.
Gibbs J., Cell (1991) 65:1–4.
Beck L., et al., Journal of Cell Biology (1988) 107:1307–1316.
Bruss V., et al., Journal of Virology (1991) 65(7):3813–3820.
Glenn J., et al., Journal of Virology (1991) 65(5): 2357–2361.
Glenn J., et al., Science (1992) 256:1331–1333.
Glomset J., et al., TIBS Reviews (1990) pp. 139–142.
Hancock J., et al., Cell (1989) 57:1167–1177.
Maltese W., FASEB Journal (1990) 4:3319–3328.
Moores S., et al., The Journal of Biological Chemistry (1991) 266(22):14603–14610.
Reiss Y., et al., Cell (1990) 62:81–88.
Schafer W., et al., Science (1989) 245: 379–385.
Wang C., et al., Journal of Virology (1991) 65:6630–6636.
Rightsel et al Nature (1964) 204:1333–1334.
Van der Pyl et al J. Antibiotics (1992) 45:1802–1805.
Detroy et al J. Gen. Micro. (1975) 92:167–174.
Miura et al. FEBS Letters (1993) 318:88–90.

Primary Examiner—Robert A. Wax
Assistant Examiner—G. E. Bugaisky
Attorney, Agent, or Firm—Morrison & Foerster

[57] ABSTRACT

Viral morphogenesis, in particular hepatitis D viral morphogenesis, may be inhibited by effecting inhibition of prenylation of at least one viral protein. The use of inhibitors of prenylation, in particular, inhibitors of the mevalonic synthesis pathway and mimics of the prenylation target CXXX (SEQ ID NO:1) box are disclosed.

6 Claims, 2 Drawing Sheets

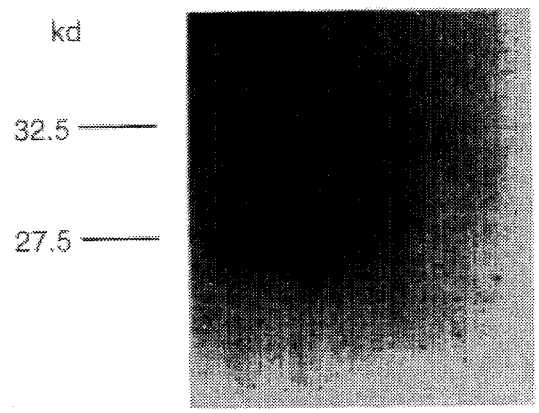
FIG._1A
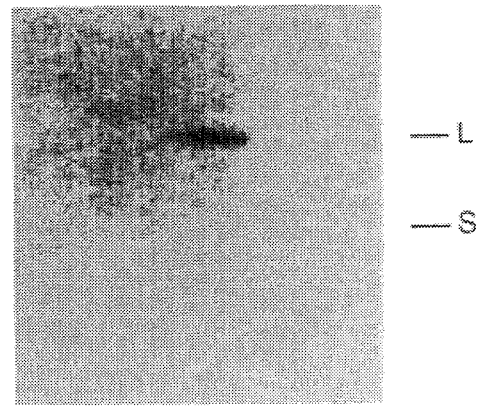
FIG._1B
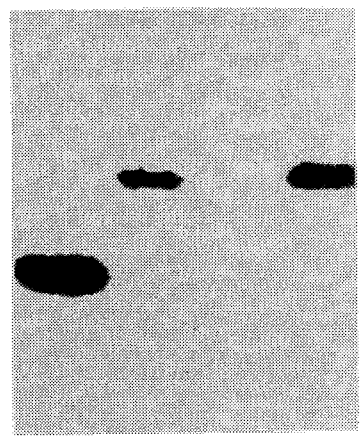
FIG._2A
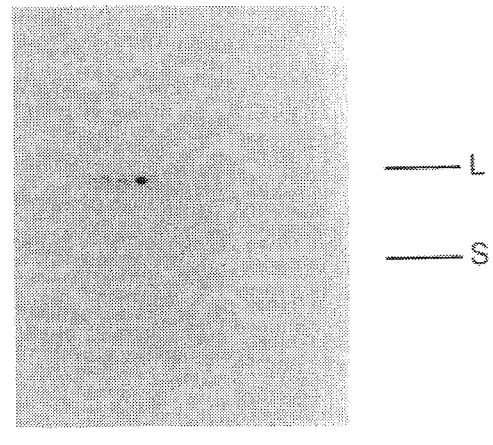
FIG._2B

FIG._3A
FIG._3C
FIG._3B
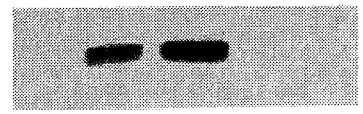
FIG._3D
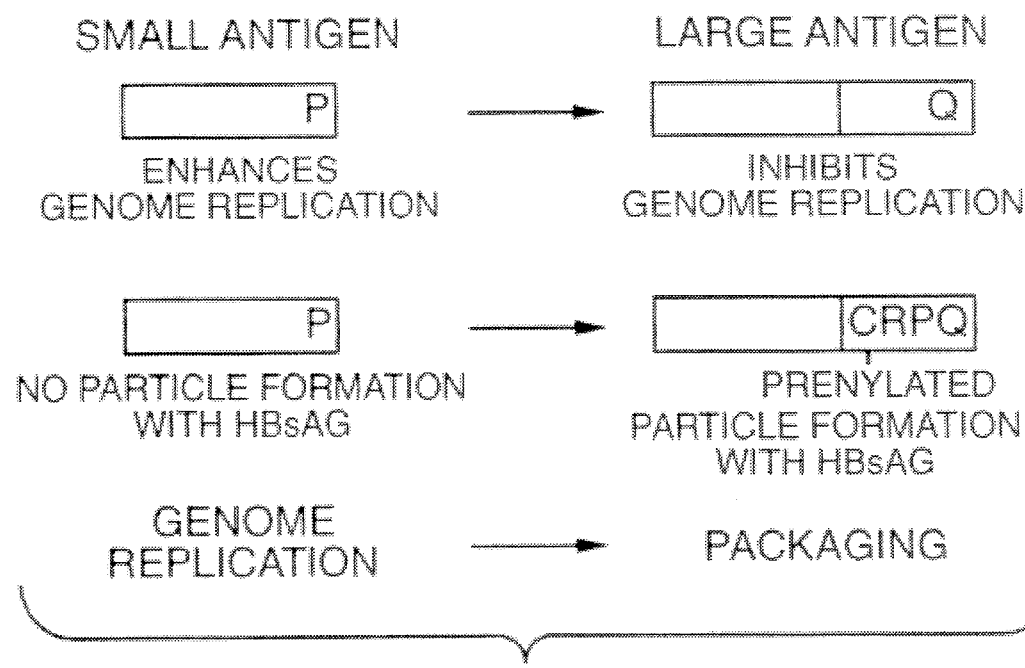
FIG._4

METHOD FOR INHIBITION OF VIRAL MORPHOGENESIS

This invention was made with the support of the National Institutes of Health. The United States Government has certain rights in this invention.

TECHNICAL FIELD

The invention is directed to inhibiting viral morphogenesis and viral infection. In particular, it concerns effecting such inhibition by inhibiting the prenylation of a viral protein.

BACKGROUND ART

It has been shown that certain membrane-associated proteins require the addition of lipophilic residues in order to function properly. One family of such modifications is termed "prenylation" because the hydrophobic residue is derived from isoprenoid precursors. The prenyl residue is known to attach to the sulfhydryl group of a cysteine which has been shown in a number of membrane-associated proteins to be contained in a "CXXX" (SEQ ID NO:1) box at the carboxy terminus of the substrate protein. In particular, such membrane-associated proteins have been shown to be associated with a protein product of the ras oncogene. Summaries of these reactions conferring hydrophobic properties on membrane enzymes, including prenylation, have appeared by Hoffman, M., *Science* (1991) 254:650–651, and by Gibbs, J. B., *Cell* (1991) 65:1–4.

In the prenylation substrate proteins studied to date, the CXXX (SEQ ID NO:1) box contains aliphatic residues in the second and third positions and a leucine, serine, methionine, cysteine or alanine in the terminal position. Thus, in the CXXX (SEQ ID NO:1) boxes so far studied, the box itself is relatively hydrophobic.

It has now been found that prenylation of a viral protein is necessary for the morphogenesis of HDV virus. The viral protein which is the target of prenylation, surprisingly, contains a hydrophilic CXXX (SEQ ID NO:1) box of the sequence Cys-Arg-Pro-Gln (SEQ ID NO:2). This relatively hydrophilic CXXX (SEQ ID NO:1) box and corresponding CXXX (SEQ ID NO:1) boxes (hydrophilic or otherwise) or other cysteine-containing sequences near the C-terminus of proteins in other virions are suitable targets for antiviral strategies.

DISCLOSURE OF THE INVENTION

The invention provides methods to interfere with viral morphogenesis both in vitro and in vivo. Agents which interfere with the prenylation of at least one viral protein are provided to infected cells to halt the viral infection. Such cells may be in culture or may be contained in an animal subject.

Thus, in one aspect, the invention is directed to a method to inhibit viral morphogenesis which method comprises effectively interfering with the prenylation of at least one viral protein. In another aspect, the invention is directed to an assay method for screening candidate drugs for their ability to inhibit prenylation. In a third aspect, the invention is directed to a method for treating viral infection by administering an agent effective to inhibit prenylation of a viral protein. In a preferred embodiment, the viral protein is the large delta antigen of the hepatitis D virus.

BRIEF DESCRIPTION OF THE DRAWING

FIGS. 1A and 1B are photocopies of immunoblots of proteins obtained by lysis of viral-infected cells treated with tritiated mevalonate.

FIGS. 2A and 2B are photocopies of immunoblots of proteins derived from lysates of cells containing mutated viruses and labeled with tritiated mevalonate.

FIGS. 3A, 3B, 3C and 3D are photocopies of immunoblots of various cells infected with virus.

FIG. 4 is a diagrammatic representation of the progress of HDV morphogenesis.

MODES OF CARRYING OUT THE INVENTION

Hepatitis delta virus (HDV) infections cause both acute and chronic liver disease and can be fatal (1, 2). This RNA virus contains a 1.7 kb single-stranded circular genome and delta antigen, the only known HDV-encoded protein. These elements are encapsulated by a lipid envelope in which hepatitis B virus surface antigens are embedded (3), which explains why HDV infections occur only in the presence of an accompanying HBV infection (4, 5). Two isoforms of delta antigen exist in infected livers and serum (6, 7). This heterogeneity arises from a unidirectional mutation at a single nucleotide in the termination codon for delta antigen (codon 196: UAG→UGG), which occurs during replication (8). Thus, although small delta antigen is 195 amino acids long, large delta antigen is identical in sequence except that it contains an additional 19 amino acids at its COOH terminus. Although both forms of delta antigen contain the same RNA genome binding domain (9), they have dramatically different effects on genome replication. The small form is required for replication, whereas the large form is a potent trans-dominant inhibitor (10, 11).

The last four amino acids of large delta antigen are Cys-Arg-Pro-Gln-COOH (SEQ ID NO:3). This COOH-terminal configuration, termed a CXXX (SEQ ID NO:1) box (where C is cysteine and X is any amino acid), has been implicated as a substrate for prenyltransferases that add to the cysteine 15 (farnesyl) or 20 (geranylgeranyl) carbon moieties derived from mevalonic acid (12–14). The resulting hydrophobic modification may aid in membrane association of the derivatized protein, as suggested for p21 Ras (15, 16) and lamin B (12, 17). We have now demonstrated that large delta antigen is similarly modified.

Other virions also contain suitable target sequences for prenylation. These sequences are near the carboxy terminus of the viral protein targeted, and may be in the form of CXXX (SEQ ID NO:1) boxes, but the cysteine may also be closer to the C-terminus, including a position as the C-terminal amino acid, as is the case in hepatitis B (HBV).

To determine whether large delta antigen is a substrate for prenylation, we labeled three cell lines, SAG, LAG, and GP4F, with [$^3$H]mevalonic acid. GP4F cells are a derivative of NIH 3T3 cells (18). SAG (19) and LAG (20) cells are derivatives of GP4F cells that stably express the small and large delta antigens, respectively.

Labeled cell lysates were analyzed on immunoblots (FIG. 1A) to detect steady-state amounts of small and large delta antigen. The lysates were also subjected to immunoprecipitation with an antibody to the delta antigens (anti-delta), SDS polyacrylamide gel electrophoresis (SDS-PAGE), and fluorography (FIG. 1B).

In more detail, referring to FIG. 1, large delta antigen is shown to be prenylated in cultured cells. The cell lines SAG

(19) (lane 1), LAG (20) (lane 2), and GP4F (18) (lane 3) were grown overnight in Lovastatin (25 μM) and (R,S)-[5-$^3$H]mevalonate (140 mM)) (30), and lysed in RIPA buffer [50 mM Tris (pH 7.5), 150 mM NaCl, 1% NP-40, 0.5% sodium deoxycholate, 0.1% SDS) (20). (A) Aliquots were subjected to immunoblot analysis (11). The blot was treated with serum from an HDV-infected patient that contained antibody to delta antigen (α-δAg) and horseradish peroxidase-conjugated rabbit antibody to human immunoglobulin A (IgG) (Promega), followed by chemiluminescence (Amersham) development. (B) Immunoprecipitates (with α-δAg) from cell extracts were subjected to SDS-PAGE and fluorography, S, small delta antigen, L, large delta antigen. Molecular size markers are shown at the left (in kilodaltons).

Thus, the large, but not the small, antigen was labeled with [$^3$H]mevalonic acid, suggesting that large delta antigen undergoes prenylation in cultured cells.

We obtained similar results using in vitro translation reactions (13) performed in the presence of [$^3$H]proline or [$^3$H]mevalonate (FIG. 2). FIG. 2. also shows mutation of $Cys^{211}$ of large delta antigen to Ser and loss of prenylation. In vitro translation reactions were performed with rabbit reticulocyte lysates (Promega) in the presence of either (A) L-[2,3,4,5-$^3$H]proline (19 μM) (94 Cl/mmol, Amersham) or (B), translation reactions contained small delta antigen mRNA (lane 1); large delta antigen mRNA (lane 2); water (lane 3); or large delta antigen ($Cys^{211} \rightarrow Ser$) (20) (lane 4) mRNA. A portion (20 μl) of each reaction was added to 1 ml of RIPA buffer, immunoprecipitated with α-δAg, and analyzed as described (FIG. 1).

Both the small and the large antigens were labeled with [$^3$H]proline (FIG. 2A), whereas only the large isoform was labeled with [$^3$H]mevalonate (FIG. 2B). To determine whether modification by [$^3$H]mevalonate was dependent on the presence of $Cys^{211}$ in the terminal CXXX (SEQ ID NO:1) box, we constructed a mutant that contains a serine at this position (20). $Cys^{211}$ is the only cysteine in large delta antigen. Mutating $Cys^{211}$ to Ser did not interfere with the synthesis of large delta antigen (FIG. 2A) but abolished its modification by [$^3$H]mevalonate (FIG. 2B).

The specific type of mevalonate modification of large delta antigen appears to be geranylgeranyl rather than farnesyl (21). Although the first described CXXX (SEQ ID NO:1) boxes contained aliphatic residues at the first and second positions after Cys, other types of amino acids can be found in prenylation sites (13, 14). It is not clear whether the COOH-terminal sequence Cys-Arg-Pro-Gln-COOH (SEQ ID NO:3), which differs from that of previously described CXXX (SEQ ID NO:1) boxes, implies the existence of a novel prenylation enzyme or whether it reflects a broader substrate specificity of known prenyltransferases.

For HDV particle formation, delta antigen and associated genomes are presumably targeted to cell membranes that contain HBV envelope proteins. We hypothesized that prenylation of large delta antigen could be involved in this process. We first examined whether large delta antigen was sufficient for HDV-like particle formation. HBV surface antigen (HBsAg) was expressed transiently in COS-7 cells together with small or large delta antigen. Virus-like particles consisting of delta antigen packaged into HBsAg-containing envelopes were analyzed by immunoprecipitation of clarified media supernatants with an antibody to HBsAg (anti-HBs).

FIG. 3 shows particle formation with large delta antigen and HBsAg parts (A) and (B). COS-7 cells were transiently transfected with the following plasmids: SV24H, which expresses HBV surface antigen (31), and SVLAg, which expresses small delta antigen (19) (lane 1); SV24H and SVL-large, which expresses large delta antigen (20) (lane 2); and calcium phosphate precipitate without DNA (lane 3). In (C) and (D), COS-7 cells were transfected with SV24H and SVL-large (lane 4); SV24H and SVL-large ($Ser^{211}$) (20) (lane 5); and calcium phosphate precipitate without DNA (lane 6). For (A) and (C), 48 hours after transfection, HBsAg-containing particles were immunoprecipitated from 2-ml aliquots of clarified media supernatants with anti-HBs (31) and subjected to immunoblot (with α-δAg) and chemiluminescence analyses as described (FIG. 1). For (B) and (D), the transfected cells were harvested in cell lysis buffer [50 mM Tris (pH 8.8), 2% SDS] with protease inhibitors (20), and aliquots subjected to protein immunoblot and chemiluminescence analyses. Molecular size markers are shown at the left.

The presence of delta antigen in the immunoprecipitates was assayed by immunoblot analysis (FIG. 3A). Although both small and large antigens were synthesized in the transfected cells (FIG. 3B), only the large isoform was incorporated into secreted HBsAg-containing particles (FIG. 3A). Similar selective packaging has been observed (22).

We then examined the function of mevalonate modification in this particle formation. One explanation for the preferred packaging of large delta antigen is that the small antigen lacks the CXXX box and therefore cannot undergo modification The $Cys^{211} \rightarrow Ser$ mutant of large delta antigen should behave like small delta antigen and not be packaged. This was indeed found to be the case. Whereas both wild-type and $Ser^{211}$ mutant large antigens were synthesized in transfected cells (FIG. 3D), only the wild-type form was packaged into particles (FIG. 3C). Thus, the mutated form of large delta antigen is not prenylated and cannot form particles with HBsAg.

Our results suggest that prenylation of large delta antigen is required for the formation and release of particles containing delta antigen and HBV surface antigens. The requirement of a prenylation site for productive viral infection is further suggested by other mutations of the CXXX (SEQ ID NO:1) box (23) and by the conservation of $Cys^{211}$ and a CXXX (SEQ ID NO:1) box motif among all sequenced HDV isolates (24).

The ability of large, but not small, delta antigen to be prenylated and packaged into virus particles further highlights the significance of the mutation-induced heterogeneity at the termination codon of the small delta antigen. During HDV replication, S genomes (encoding the small antigen) mutate to L genomes (encoding the large antigen). At least two effects attributable to this mutation can be distinguished (see FIG. 4). FIG. 4 shows the regulatory switch of S genomes to L genomes. During replication, S genomes encoding the small delta antigen mutate to L genomes, which encode the large delta antigen. This single base mutation has two effects on the COOH-terminus of delta antigen. The first is to change the nature of the COOH-terminal amino acid; Pro (P), which enhances genome replication (20), is replaced by Gln (Q), resulting in inhibition of genome replication. The second effect is the creation of a target prenylation site (CRPQ) (SEQ ID NO:3), C, cysteine; R, arginine; P, proline; Q, glutamine.

Thus, the first effect is the conversion of an enhancer of genome replication (small delta antigen) into a potent trans-dominant inhibitor (large delta antigen) (10, 11). This dramatic difference in function appears to be determined solely by the nature of the COOH-terminal amino acid with proline being sufficient to confer enhancer activity (11, 25). The second effect is the addition of a CXXX (SEQ ID NO:1) box to delta antigen, which allows the protein to be prenylated and presumably promotes its incorporation into HBsAg-containing particles. The combined effects of the switch from production of small to large delta antigen thus appear to have two roles: to suppress further genome replication and to promote the onset of packaging and virion morphogenesis.

Our results suggest prenylation as a new target for anti-HDV therapy and for antiviral therapy with respect to other viruses with prenylated proteins. In light of the increasingly apparent degeneracy of the four C-terminal amino acids required to function as a prenylation substrate, a cysteine located at any of these C-terminal positions is also considered a potential target of antiprenylation therapy.

Several strategies designed to interfere with the prenylation stage of the HDV life cycle may be considered, including drugs that inhibit enzymes along the prenylation pathway, and CXXX (SEQ ID NO:1) box analogs. Both therapies have been considered for the inhibition of ras-mediated oncogenic transformation (26). Tetrapeptides that correspond to the CXXX (SEQ ID NO:1) box of p21 Ha-Ras inhibit prenylation of p21 Ha-Ras in vitro (27). Finally, the dual function of large delta antigen in the HDV life cycle suggests a further refinement of a proposed (11) defective interfering particle-(DIP) (28) like therapy aimed at cells infected with actively replicating S genomes. Because L genomes require a source of small delta antigen for replication (19, 29) but, once replicated, produce a potent trans-dominant inhibitor of further replication, a therapeutically administered L genome DIP could be specific for infected cells, as well as possess an inherent shut-off mechanism (11). If the L genome also contained the $Cys^{211}$ to Ser mutation, it could encode a delta antigen that not only inhibits replication but also affects packaging.

Accordingly, new approaches to antiviral therapy and inhibition of viral morphogenesis focus on inhibition of the prenylation of at least one viral protein. This may be effected by contacting cells infected with the target virus with an effective amount of an agent which inhibits the prenylation of at least one viral protein. Such agents include inhibitors of formation of the prenyl residue precursors which are derivative of the mevalonate synthesis pathway. Other agents include decoys for the target sequence for prenylation including small peptides, including tetrapeptides which mimic the surroundings of the cysteine residue to be prenylated. As set forth above, the cysteine residue to be prenylated is generally found at the carboxy terminus of the target protein; although the most common target sequence involves a CXXX (SEQ ID NO:1) box, cysteines positioned closer to the C-terminus may also be targeted; thus, the relevant peptides may include those of the form XCXX, XXCX, and XXXC (SEQ ID NO:4,SEQ ID NO:5and SEQ ID NO:6). Other suitable agents include inhibitors of the prenyltransferase enzymes.

If viral morphogenesis is to be inhibited in culture, suitable host cells are used to culture the virus, and the agents used in inhibiting prenylation added to the medium. If the infected cells are contained in an animal subject, such as a mammalian subject or in particular a human or other primate subject, the agent used for the prenylation inhibition is generally introduced as a pharmaceutical formulation. Suitable formulations depending on the nature of the agent chosen may be found in *Remington's Pharmaceutical Sciences*, latest edition, Mack Publishing Co., Easton, Pa. The routes of administration include standard such routes, including administration by injection, oral administration, and transmucosal and transdermal administration. The choice of formulation will depend on the route of administration as well as the agent chosen. Suitable mixtures of agents can also be used as active ingredients.

The invention is also directed to a method to screen candidate drugs as prenylation inhibitors which method comprises contacting cells which secrete or which have been modified to secrete HDV large delta antigen and a control antigen, wherein secretion of said large delta antigen is dependent on prenylation and secretion of said control antigen is not dependent on prenylation, with said candidate drug under conditions wherein said control antigen is secreted, and determining the presence, absence or amount of said large delta antigen secreted from said cells, wherein a candidate drug which decreases or abolishes the amount of secreted large delta antigen is said effective prenylation inhibitor.

The following references are listed according to the number which refers to them in the body of the specification:

REFERENCES AND NOTES

1. M. Rizzetto, *Hepatology* 3, 729 (1983).
2. J. H. Hoffnagle, *J. Am. Med. Assoc.* 261, 1321 (1989).
3. F. Bonino et al., *Infect. Immun.* 43, 1000 (1984).
4. M. Rizzetto et al., *J. Infect. Dis.* 141, 590 (1980).
5. M. Rizzetto et al., *Proc. Natl. Acad. Sci. U.S.A.* 77, 6124 (1980).
6. K. F. Bergmann and J. L. Gerin, *J. Infect. Dis.* 154, 702 (1986).
7. F. Bonino, K. H. Heermann, M. Rizzetto, W. H. Gerlich, *J. Virol.* 58, 945 (1986).
8. G. Luo et al., ibid. 64, 1021 (1990).
9. J. -H. Lin, M. -F. Chang, S. C. Baker, S. Govindarjan, M. M. C. Lai, ibid., p. 4051.
10. M. Chao, S. -Y. Hsieh, J. Taylor, ibid., p. 5066.
11. J. S. Glenn and J. M. White, ibid, 65, 2357 (1991).
12. J. A. Glomset, M. H. Gelb, C. C. Farnsworth, Trends Biochem. Sci. 15, 139 (1990).
13. W. A. Maltese, *FASEB J.* 4, 3319 (1990).
14. S. L. Moores et al., *J. Biol. Chem.* 266, 14603 (1991).
15. J. F. Hancock. A. I. Magee, J. E. Childs, C. J. Marshall, *Cell* 57, 1167 (1989).
16. W. R. Schafer et al., *Science* 245, 379 (1989).
17. L. A. Beck, T. J. Hosiak, M. Sinensky, *J. Cell Biol.* 107, 1307 (1988).
18. H. Ellens, S. Doxsey, J. S. Glenn, J. M. White, *Methods Cell Biol.* 31, 156 (1989).
19. J. S. Glenn, J. M. Taylor, J. M. White, *J. Virol.* 64, 3104 (1990). SAG cells are identical to GAG cells.
20. J. S. Glenn, thesis, University of California, San Francisco (1992).
21. J. S. Glenn, J. A. Watson, C. M. Havel, J. M. White, unpublished data.
22. C. J. Wang, P. J. Chen, J. C. Wu, D. Patel, D. S. Chen, *J. Virol.* 65, 6630 (1991); W. S. Ryu, M. Bayer, J. Taylor, ibid., in press; C. Sureau, personal communication.
23. W. S. Ryu, J. S. Glenn, J. M. White, J. Taylor, in preparation.
24. Of 14 independent viral isolates sequenced, 13 code for Cys-Arg-Pro-Gln-COOH and 1 codes for Cys-Thr-Pro-Gln-COOH as the four terminal amino acids of large delta antigen [K. -S. Wang et al., *Nature* 323, 508 (1986); S. Makino et al., ibid. 329, 343 (1987); M. Y. P. Kuo et al., *J. Virol*, 62, 1855 (1988); J. A. Saldanna, H. C. Thomas, J. P. Moniardino, *J. Gen. Virol.* 71, 1603 (1990); Y. -P. Xia, M. -F. Chang. D. Wei, S. Govindarjan, M. M. C. Lai, *Virology* 178, 331 (1990); F. Imazeki, M. Omata, M. Ohto, *J. Virol.* 64, 5594 (1990); Y. -C. Chao, C. -M. Lee, H. -S. Tang. S. Govindarjan, M. M. C. Lai, *Hepatology* 13, 345 (1991); P. Derry et al., *J. Gen. Virol.* 72, 735 (1991)].
25. We have recently found that specific mutation of the COOH-terminal Gln of large delta antigen to Pro converted the protein from an inhibitor to an enhancer of genome replication (20).
26. J. B. Gibbs, *Cell* 65, 1 (1991).
27. Y. Reiss, J. L. Goldstein, M. C. Seabra, P. J. Casey, M. S. Brown, ibid. 62, 81 (1990).
28. R. F. Ramo, in Virology, B. N. Fields et al., Eds. (Raven, N.Y., 1990), pp. 112–122.
29. M. Y. -P. Kuo, M. Chao, J. Taylor, *J. Virol.* 63, 1945 (1989).
30. (R,S)-[5-$^3$H]mevalonate (4 to 18.8 Ci/mmol) was synthesized according to the method of R. K. Keller, *J. Biol. Chem.* 261, 12053 (1986).
31. V. Bruss and D. Ganem, *J. Virol.* 65, 3813 (1991).
32. We thank J. -J. Gonvers for providing human anti-delta antigen serum, A. Alberts for providing Lovestatin, D. Ganem for providing the anti-HBs and SV24H, and J. M. Bishop, H. Bourne, and D. Ganem for helpful discussions and critical reading of the manuscript, J. M. W. is a recipient of an NIH grant and J. S. G. was supported by the Medical Scientist Training Program.

I claim:

1. A method to inhibit morphogenesis of hepatitis D virus (HDV) which method comprises preventing or inhibiting the prenylation of the large delta antigen of said HDV by contacting cells infected with HDV with an amount of an agent effective to directly inhibit the prenylation of said large delta antigen;

wherein said agent mimics the amino acid sequence Cys-Arg-Pro-Gln (SEQ ID NO:2) as it occurs in the large delta antigen; or wherein said agent is an inhibitor of enzymes along the pathway of prenyl lipid synthesis from mevalonate; or wherein said agent is an inhibitor of a prenyl transferase.

2. The method of claim 1 wherein said cell is contained in an animal subject and said contacting comprises administering said agent to said subject.

3. The method of claim 1 wherein said agent mimics the amino acid sequence Cys-Arg-Pro-Gln (SEQ ID NO:2) as it occurs in the large delta antigen.

4. The method of claim 1 wherein said agent is an inhibitor of enzymes along the pathway of prenyl lipid synthesis from mevalonate.

5. The method of claim 1 wherein said agent is an inhibitor of a prenyl transferase.

6. A method to screen candidate drugs as prenylation inhibitors which method comprises contacting cells which secrete or which have been modified to secrete HDV large delta antigen and a control antigen, wherein secretion of said large delta antigen is dependent on prenylation and secretion of said control antigen is not dependent on prenylation, with said candidate drug under conditions wherein said control antigen is secreted, and determining the presence, absence or amount of said large delta antigen secreted from said cells, wherein a candidate drug which decreases or abolishes the amount of secreted large delta antigen is said effective prenylation inhibitor.

* * * * *

UNITED STATES PATENT AND TRADEMARK OFFICE
CERTIFICATE OF CORRECTION

PATENT NO.   : 5,503,973
DATED        : April 2, 1996
INVENTOR(S)  : Jeffrey S. Glenn It is certified that error appears in the above-identified patent and that said Letters Patent is hereby corrected as shown below:

Title page,
Line [73] Assignee, delete "The Regents of the University of California, Oakland, Calif." and insert -- Jeffrey S. Glenn, Palo Alto, Calif.--.

Signed and Sealed this

Eighteenth Day of September, 2001

*Attest:*

NICHOLAS P. GODICI
*Attesting Officer*    *Acting Director of the United States Patent and Trademark Office*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

Cys Xaa Xaa Xaa
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

Cys Arg Pro Gln
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 4
        ( D ) OTHER INFORMATION: /note="This position is Gln-COOH."

( x i ) SEQUENCE DESCRIPTION: SEQ ID NO:3:

Cys Arg Pro Gln
    1

( 2 ) INFORMATION FOR SEQ ID NO:4:

( i ) SEQUENCE CHARACTERISTICS:
        ( A ) LENGTH: 4 amino acids
        ( B ) TYPE: amino acid (C) STRANDEDNESS: single
    (D) TOPOLOGY: linear (x i) SEQUENCE DESCRIPTION: SEQ ID NO:4:

Xaa  Cys  Xaa  Xaa
   1

(2) INFORMATION FOR SEQ ID NO:5:

(i) SEQUENCE CHARACTERISTICS:
    (A) LENGTH: 4 amino acids
    (B) TYPE: amino acid
    (C) STRANDEDNESS: single
    (D) TOPOLOGY: linear (x i) SEQUENCE DESCRIPTION: SEQ ID NO:5:

Xaa  Xaa  Cys  Xaa
   1

(2) INFORMATION FOR SEQ ID NO:6:

(i) SEQUENCE CHARACTERISTICS:
    (A) LENGTH: 4 amino acids
    (B) TYPE: amino acid
    (C) STRANDEDNESS: single
    (D) TOPOLOGY: linear (x i) SEQUENCE DESCRIPTION: SEQ ID NO:6:

Xaa  Xaa  Xaa  Cys
   1